United States Patent
Kurth et al.

(10) Patent No.: US 10,329,426 B2
(45) Date of Patent: Jun. 25, 2019

(54) REJUVENATING COMPOSITIONS FOR ASPHALT APPLICATIONS AND METHODS OF MANUFACTURING THE SAME

(71) Applicant: Cargill, Incorporated, Wayzata, MN (US)

(72) Inventors: Todd L. Kurth, Maple Grove, MN (US); Scott Nivens, Minneapolis, MN (US); Christopher Patrick Stevermer, St. Louis Park, MN (US); Hassan Ali Tabatabaee, Plymouth, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/715,914

(22) Filed: Sep. 26, 2017

(65) Prior Publication Data

US 2018/0080180 A1    Mar. 22, 2018

Related U.S. Application Data

(62) Division of application No. 15/553,711, filed as application No. PCT/US2016/019790 on Feb. 26, 2016.

(Continued)

(51) Int. Cl.
| | | |
|---|---|---|
| C08L 91/00 | (2006.01) | |
| C09D 195/00 | (2006.01) | |

(Continued)

(52) U.S. Cl.
CPC ............... C08L 91/00 (2013.01); C08H 3/00 (2013.01); C08L 91/02 (2013.01); C08L 95/00 (2013.01);
(Continued)

(58) Field of Classification Search
CPC ....... C08L 95/00; C08L 91/00; C09D 195/00; C09J 195/00; C10C 3/00; E01C 7/00;
(Continued)

(56) References Cited

U.S. PATENT DOCUMENTS

| | | |
|---|---|---|
| 2,750,298 A | 6/1956 | Euchner et al. |
| 2,815,296 A | 12/1957 | Young et al. |

(Continued)

FOREIGN PATENT DOCUMENTS

| | | | |
|---|---|---|---|
| CA | 2315955 A1 | 2/2002 | |
| CA | 2571214 A1 * | 2/2006 | ........... C07D 303/42 |

(Continued)

*Primary Examiner* — Alexandra M Moore

(57) ABSTRACT

Disclosed herein are rejuvenating compositions for asphalt applications. In one aspect, the rejuvenating composition comprises a polymerized oil having a polymeric distribution ranging from about 2 to about 80 wt % oligomer content and Hildebrand solubility ranging from about 6 to about 12. In another aspect, the rejuvenating composition comprises an oil having a Hildebrand solubility ranging from about 6 to about 12 and a flash point ranging from about 100° C. to about 400° C. In yet another aspect, the rejuvenating composition comprises a modified oil having a Hildebrand solubility ranging from about 6 to about 12 and a flash point ranging from about 100° C. to about 400° C.

20 Claims, 1 Drawing Sheet

Related U.S. Application Data

(60) Provisional application No. 62/126,064, filed on Feb. 27, 2015.

(51) Int. Cl.
  *C08L 95/00* (2006.01)
  *E01C 7/26* (2006.01)
  *E01C 11/00* (2006.01)
  *C09D 7/65* (2018.01)
  *C08H 3/00* (2006.01)
  *C08L 91/02* (2006.01)
  *G01N 25/48* (2006.01)

(52) U.S. Cl.
  CPC .............. *C08L 95/005* (2013.01); *C09D 7/65* (2018.01); *C09D 195/00* (2013.01); *E01C 7/26* (2013.01); *E01C 7/262* (2013.01); *E01C 11/005* (2013.01); *C08L 2205/02* (2013.01); *C08L 2205/08* (2013.01); *C08L 2555/28* (2013.01); *C08L 2555/34* (2013.01); *C08L 2555/80* (2013.01); *C08L 2555/82* (2013.01); *G01N 25/4866* (2013.01); *Y02A 30/333* (2018.01)

(58) Field of Classification Search
  CPC ...... E01C 7/187; E01C 7/262; C10M 129/00; C11B 3/00; C11C 3/00
  See application file for complete search history.

(56) References Cited

U.S. PATENT DOCUMENTS

| | | |
|---|---|---|
| 2,817,653 A | 12/1957 | Cole et al. |
| 3,595,820 A | 7/1971 | Herder et al. |
| 4,226,552 A | 10/1980 | Moench |
| 4,740,322 A | 4/1988 | Dibiase et al. |
| 6,117,227 A | 9/2000 | Kitagawa |
| 6,133,351 A | 10/2000 | Hayner |
| 6,956,071 B2 | 10/2005 | Butler et al. |
| 6,987,207 B1 | 1/2006 | Ronyak et al. |
| 7,951,417 B1 | 5/2011 | Wen et al. |
| 8,765,985 B2 | 7/2014 | Hora et al. |
| 8,821,064 B1 | 9/2014 | Morris et al. |
| 2008/0314294 A1 | 12/2008 | White et al. |
| 2010/0034586 A1 | 2/2010 | Bailey et al. |
| 2010/0261805 A1 | 10/2010 | Abraham et al. |
| 2011/0003727 A1 | 1/2011 | Bloom et al. |
| 2012/0065417 A1 | 3/2012 | Hora et al. |
| 2012/0315088 A1 | 12/2012 | Deneuvillers et al. |
| 2013/0184383 A1 | 7/2013 | Cochran et al. |
| 2014/0083328 A1 | 3/2014 | Lochel et al. |
| 2014/0261076 A1 | 9/2014 | Quinn et al. |
| 2014/0033856 A1 | 11/2014 | Severance et al. |
| 2014/0338565 A1 | 11/2014 | Broere et al. |
| 2014/0343192 A1 | 11/2014 | Cochran et al. |

FOREIGN PATENT DOCUMENTS

| | | | |
|---|---|---|---|
| EP | 0712834 A1 | 5/1996 | |
| GB | 2462371 A | 2/2010 | |
| WO | 2009137298 A1 | 11/2009 | |
| WO | 2010016127 A1 | 2/2010 | |
| WO | WO-2010077141 A1 * | 7/2010 | .............. C08L 95/00 |
| WO | WO-2012166414 A1 * | 12/2012 | ............ C09J 103/02 |
| WO | WO-2013090283 A1 * | 6/2013 | .............. C08L 91/00 |
| WO | WO-2013163463 A1 * | 10/2013 | .............. C08L 91/00 |
| WO | 2015138958 A1 | 9/2015 | |

* cited by examiner

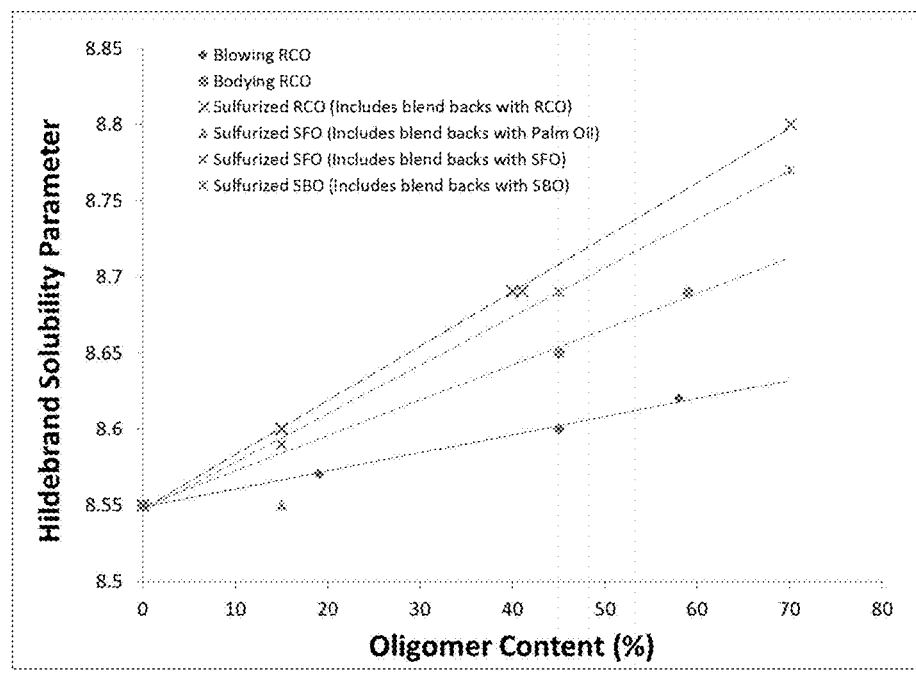

US 10,329,426 B2

REJUVENATING COMPOSITIONS FOR ASPHALT APPLICATIONS AND METHODS OF MANUFACTURING THE SAME

CROSS REFERENCE TO RELATED APPLICATION

This application claims the benefit of U.S. Provisional Application No. 62/126,064 filed on Feb. 27, 2015, which is hereby incorporated by reference in its entirety.

TECHNICAL FIELD

This disclosure relates to rejuvenating compositions for asphalt applications and methods of manufacturing the same.

BACKGROUND

Recent technical challenges facing the asphalt industry have created opportunities for the introduction of agriculture-based products for the overall performance enhancement of asphalt. Such performance enhancements may include expanding the useful temperature interval (UTI) of asphalt, rejuvenating aged asphalt, and compatibilizing the various chemical fractions in asphalt with each other as well as with other additives such as elastomeric thermoplastic polymers in asphalt.

SUMMARY

Disclosed herein are rejuvenating compositions for asphalt applications. In one aspect, the rejuvenating composition comprises a polymerized oil having a polymeric distribution ranging from about 2 to about 80 wt % oligomer content and Hildebrand solubility ranging from about 6 to about 12. In another aspect, the rejuvenating composition comprises an unmodified/non-polymerized oil having a Hildebrand solubility ranging from about 6 to about 12 and a flash point ranging from about 100° C. to about 400° C. In yet another aspect, the rejuvenating composition comprises a modified oil having a Hildebrand solubility ranging from about 6 to about 12 and a flash point ranging from about 100° C. to about 400° C.

FIGURES

FIG. 1 illustrates various oils that may be used in the rejuvenating composition and compares oligomer content against Hildebrand solubility.

DETAILED DESCRIPTION

"Flash Point" or "Flash Point Temperature" is a measure of the minimum temperature at which a material will initially flash with a brief flame. It is measured according to the method of ASTM D-92 using a Cleveland Open Cup and is reported in degrees Celsius (° C.).

"Oligomer" is defined as a polymer having a number average molecular weight (Mn) larger than 1000. A monomer makes up everything else and includes monoacylglycerides (MAG), diacylglycerides (DAG), triacylglycerides (TAG), and free fatty acids (FFA).

"Performance Grade" (PG) is defined as the temperature interval for which a specific asphalt product is designed. For example, an asphalt product designed to accommodate a high temperature of 64° C. and a low temperature of −22° C. has a PG of 64-22. Performance Grade standards are set by the America Association of State Highway and Transportation Officials (AASHTO) and the American Society for Testing Materials (ASTM).

"Polydispersity Index" (also known as "Molecular Weight Distribution") is the ratio of weight average molecular weight (Mw) to number average molecular weight (Mn). The polydispersity data is collected using a Gel Permeation Chromatography instrument equipped with a Waters 510 pump and a 410 differential refractometer. Samples are prepared at an approximate 2% concentration in a THF solvent. A flow rate of 1 ml/minute and a temperature of 35° C. are used. The columns consist of a Phenogel 5 micron linear/mixed Guard column, and 300×7.8 mm Phenogel 5 micron columns (styrene-divinylbenzene copolymer) at 50, 100, 1000, and 10000 Angstroms. Molecular weights were determined using the following standards:

| Standard | Mono-olein | Diolein | Arcol LHT 240 | Trio-lein | Epoxidized Soybean Oil | Acclaim 2200 | Multranol 3400 | Acclaim 8200 |
| --- | --- | --- | --- | --- | --- | --- | --- | --- |
| Molecular Weight (Daltons) | 356 | 620 | 707 | 878 | 950 | 2000 | 3000 | 8000 |

"Useful Temperature Interval" (UTI) is defined as the interval between the highest temperature and lowest temperature for which a specific asphalt product is designed. For example, an asphalt product designed to accommodate a high temperature of 64° C. and a low temperature of −22° C. has a UTI of 86. For road paving applications, the seasonal and geographic extremes of temperature will determine the UTI for which an asphalt product must be designed. UTI of asphalt is determined by a series of AASHTO and ASTM standard tests developed by the Strategic Highway Research Program (SHRP) also known as the "Performance Grading" (PG) specification.

Asphalt and Bituminous Materials

For the purpose of this invention asphalt, asphalt binder, and bitumen refer to the binder phase of an asphalt pavement, roofing, coatings or other industrial applications. Bituminous material may refer to a blend of asphalt binder and other material such as mineral aggregate or filler. The binder used in this invention may be material acquired from asphalt producing refineries, flux, refinery vacuum tower bottoms, pitch, and other residues of processing of vacuum tower bottoms, as well as oxidized and aged asphalt from recycled bituminous material such as reclaimed asphalt pavement (RAP), and recycled asphalt shingles (RAS) or in the surface layer of existing pavements.

For the purpose of this invention, emulsion is defined as a multiphase material in which all phases are dispersed in a continuous aqueous phase. The aqueous phase may be comprised of surfactants, acid, base, thickeners, and other additives. The dispersed phase may comprise of the polymerized oil, thermoplastic natural and synthetic polymers, waxes, asphalt, and other additives and oils, herein collectively referred to as the "oil phase". High shear and energy is often necessary to disperse the oil phase in the aqueous phase using apparatus such as colloidal mills.

Description of Oil

The rejuvenating composition for asphalt applications described herein comprises an oil. The oil in the rejuvenation composition may be a biorenewable oil (unmodified/non-polymerized), a petroleum based oil (unmodified/non-polymerized), or polymerizations or modifications thereof.

Biorenewable oils can include oils isolated from plants, animals, and algae.

Examples of plant-based oils may include but are not limited to soybean oil, linseed oil, canola oil, rapeseed oil, castor oil, tall oil, cottonseed oil, sunflower oil, palm oil, peanut oil, safflower oil, corn oil, corn stillage oil, lecithin (phospholipids) and combinations, distillates, derivatives, and crude streams thereof.

Examples of animal-based oils may include but are not limited to animal fat (e.g., lard, tallow) and lecithin (phospholipids), and combinations, distillates, derivatives, and crude streams thereof.

Biorenewable oils can also include partially hydrogenated oils, oils with conjugated bonds, and bodied oils wherein a heteroatom is not introduced, for example but not limited to, diacylglycerides, monoacylglycerides, free fatty acids (and distillate streams thereof), alkyl esters of fatty acids (e.g., methyl, ethyl, propyl, and butyl esters), diol and triol esters (e.g., ethylene glycol, propylene glycol, butylene glycol, trimethylolpropane), and mixtures and derivative streams thereof. An example of biorenewable oils may be waste cooking oil or other used oils.

Petroleum based oil includes a broad range of hydrocarbon-based compositions and refined petroleum products, having a variety of different chemical compositions which are obtained from recovery and refining oils of fossil based original and considered non-renewable in that it takes millions of year to generate crude starting material.

The aforementioned biorenewable or petroleum based oils may be polymerized wherein polymerization is achieved through crosslinking of the fatty acid chains and/or the glyceride fraction of the tri-glyceride molecules contained in the starting oil material utilizing sulfurization, bodying, blowing, or polyol ester (for example, polyglycerol ester or a castor oil ester, or estolides) polymerization techniques to achieve a targeted oligomerization and/or Hildebrand solubility parameter. It shall also be understood that polymerized oil versions may also be blended with straight (i.e., non-polymerized/unmodified) biorenewable or petroleum based oil or modified variations thereof.

Modified oils can include biorenewable or petroleum based oils modified utilizing maleic anhydride, acrylic acid, hydrogen, dicyclopentadiene, a conjugation via reaction with iodine, or interesterification.

Despite the oil utilized in the rejuvenating composition (biorenewable oil, petroleum based, or polymerization or modifications thereof), the oil has a Hildebrand solubility ranging from about 6 to about 12. FIG. 1 illustrates various oils that may be used in the rejuvenating composition and compares oligomer content against Hildebrand solubility.

Further, the oil utilized in the rejuvenating compositions has a flash point, as measured using the Cleveland Open Cup method, of at least about 100° C. and no more than about 400° C. In some aspects, the flash point is between about 200° C. and about 350° C. In other aspects, the flash point is between about 220° C. and about 300° C. In yet other aspects, the flash point is between about 245° C. and about 275° C.

Specifically regarding a polymerized version of biorenewable or petroleum based oil, the viscosity of the polymerized oil will vary based on the type of starting oil material, but generally ranges from about 1 cSt to about 100 cSt at 100° C. Further, the polymeric distribution ranging from about 2 wt % and about 80 wt % oligomers (20 wt % to 98 wt % monomers), and more preferably between about 15 wt % to about 60 wt % oligomers (40 wt % to 85 wt % monomers), and even more preferably between about 20 wt % to about 60 wt % oligomers (40 wt % to 80 wt % monomers) is achieved. In even more preferred aspects, the polymeric distribution ranges from about 50 wt % to about 75 wt % oligomers and about 25 wt % to about 50 wt % monomers.

Rejuvenation of Aged Bituminous Material

Asphalt "ages" through a combination of mechanisms, mainly oxidation and volatilization. Aging increases asphalt modulus, decreases viscous dissipation and stress relaxation, and increases brittleness at lower performance temperatures. As a result, the asphalt becomes more susceptible to cracking and damage accumulation. The increasing usage of recycled and reclaimed bituminous materials which contain highly aged asphalt binder from sources such as reclaimed asphalt pavements (RAP) and recycled asphalt shingles (RAS) have created a necessity for "rejuvenators" capable of partially or completely restoring the rheological and fracture properties of the aged asphalt. Aging of asphalt has also been shown to increase colloidal instability and phase incompatibility, by increasing the content of high molecular weight and highly polar insoluble "asphaltene" fraction which may increasingly associate. The use of the oils described herein are particularly useful for RAP and RAS applications. The oils described in this document act as a compatibilizer of the asphalt fractions, especially in aged and oxidized asphalt, resulting in a balanced and stable asphalt binder with restored performance and durability.

During plant production the asphalt is exposed to high temperatures (usually between 150 to 190° C.) and exposure to air during which significant oxidation and volatilization of lighter fractions can occur leading to an increase in modulus and a decrease in viscous behavior. The aging process is simulated using a Rolling Thin Film Oven (ASTM D2872) during which a rolling thin film of asphalt is subjected a jet of heated air at about 163° C. for about 85 minutes. The rheological properties are measured before and after the aging procedure using a Dynamic Shear Rheometer following ASTM D7175 using the ratio of the $|G^*|/\sin \delta$ after to before aging, in which $G^*$ is the complex modulus and $\delta$ is the phase angle. The larger the ratio of the $(|G^*|/\sin \delta)$ after aging to the $(|G^*|/\sin \delta)$ before aging, the higher the effect of oxidative aging and volatilization on the tested asphalt.

Using this procedure it is shown that asphalts treated with the oils described herein have a lower ratio, thus showing a lower tendency for change in rheological properties as a result of oxidative aging and volatilization.

Accordingly, the oils described herein have been shown to be capable of rejuvenating aged asphalt binder, and modify the rheological properties of the asphalt binder. As a result, small dosages of the oil can be used to incorporate high content of aged recycled asphalt material into pavements and other applications resulting in significant economic savings and possible reduction in the environmental impact of the pavement through reduction of use of fresh resources.

Additional components may be added to the oil described herein, for example but not limited to thermoplastic elastomeric and plastomeric polymers, polyphosphoric acid, anti-stripping additives, warm mix additives, emulsifiers, and/or fibers.

Notably, the oils described herein may be used to make an emulsion for use in asphalt rejuvenation applications. The emulsion comprises an oil phase and an aqueous phase. The oil phase comprises the oil described herein and may further comprise of asphalt binder and other additives and modifiers, wherein the oil is about 0.1 to 100 wt % of the oil phase. The aqueous phase often comprises a surfactant and may further comprise natural and synthetic polymers (such as Styrene Butadiene Rubber and latex) and/or water phase thickeners.

The oil phase makes up about 15 to 85 wt % of the emulsion with the aqueous phase making up the remaining balance. It is understood by those skilled in the art that emulsions are sometimes further diluted with water at time of application, thus the effective oil phase content of the diluted emulsion may be reduced indefinitely.

Further contemplated herein is a method comprising applying the emulsion to the surface of an existing pavement or applying the emulsion to treat RAS or RAP and further mixing the treated RAS or RAP with virgin asphalt thereby obtaining a rejuvenated asphalt blend.

The emulsion may also be used as part of a cold patching material, a high performance cold patch or cold mix application that contains recycled asphalt thereby obtaining treated RAS or RAP.

In other aspects, the emulsion may be used for cold-in-place recycling of milled asphalt pavements or hot-in-place recycling of milled asphalt pavements.

EXAMPLES

The following examples are presented to illustrate the present invention and to assist one of ordinary skill in making and using same. The examples are not intended in any way to otherwise limit the scope of the invention.

Experimental Method

A charge of precipitated sulfur (mass ranges between 6.5 grams to 56.5 grams) is added to a 1 liter round bottom flask containing 650 grams of biorenewable oil. The reactor is then heated to the target reaction temperature using a heating mantle, taking care not to over shoot the target temperature by more than 5° C. The reaction mixture is agitated using a motorized stirrer with a stir shaft and blade. The reaction is continuously sparged with nitrogen at 2-12 standard cubic feet per hour (SCFH). A condenser and receiving flask is used to collect any distillate.

It is noted that the reaction will create foam around 110-115° C. when the sulfur melts into the oil. The reaction is monitored using GPC, to measure the oligomer content and distribution, and viscosity is measured at 40° C. following ASTM D445. The reaction is considered complete when the desired oligomer content and Polydispersity Index has been achieved. The reactor is then cooled to 60° C.

Example 1: Cationic Emulsion of Asphalt Containing Sulfurized Soybean Oil Blend #1

A modified asphalt binder comprising:
95.0% by weight of neat asphalt binder graded as PG64-22 (PG 64.88-24.7)
5.0% by weight of a blend having:
   59.0% by weight of a sulfurized soybean oil reacted with 7.0% by weight of elemental sulfur at 160° C. for 19 hrs under a Nitrogen sparge. This resulted in a modifier with 70.8% oligomer
   41.0% by weight of straight soybean oil
   Blend of the sulfurized oil and the soybean oil had about 45.6% oligomer content and a PDI of approximately 3.95.

The modifier was blended into the asphalt after the binder had been annealed at 150° C. for 1 hour.

The modified asphalt was used as the oil component to make a latex modified cationic rapid set emulsion. The oil phase was 65.0% by total weight of the emulsion. The aqueous phase consisted of the following components:
   0.70% by weight of emulsion of a cationic quick set imidazoline emulsifier (Anova 1620 manufactured by Cargill)
   2.0% by weight of emulsion of Latex (UltraPave)
   HCl in sufficient content to achieve a pH of 2.6

Incorporation of the polymerized oil in this formulation enables use of this product in rejuvenating surface applications used for pavement maintenance and preservation, especially rejuvenating scrub seal applications, and rejuvenating fog seals and sand seals. Furthermore, the emulsified solution enables use in low unheated paving applications (known as "Cold Mixes") such as cold in place recycling, cold patch, and cold mix pavement layers. Use of rapid-setting surfactant formulations, such as that used in this example, enable rapid buildup of aggregate retention and traffic resistance. As a result, in ideal conditions the road can be opened to traffic within 30 minutes to an hour of the application. The content of polymerized oil will vary depending on the grade of the base oil and the final desired properties.

Example 2: Cationic Emulsion of Asphalt Containing a Sulfurized Soybean Oil and Recovered Corn Oil Blend This example demonstrates the use of another polymerized oil that may be used in applications similar to that described in Example #1.

A modified asphalt binder comprising:
95.0% by weight of neat asphalt binder graded as PG64-22 (PG 64.88-24.7)
5.0% by weight of a blend having:
   59.0% by weight of a sulfurized soybean oil reacted with 7.0% by weight of elemental sulfur at 160° C. for 19 hrs under a Nitrogen sparge. This resulted in a modifier with 70.8% oligomer
   41.0% by weight of recovered corn oil
   Blend of the sulfurized oil and the recovered corn oil had about 46.31% oligomer content and a PDI of approximately 4.40.

The modifier was blended into the asphalt after the binder had been annealed at 150° C. for 1 hour.

The modified asphalt was used as the oil phase in a latex modified cationic rapid set emulsion. The oil phase was 65.0% by total weight of the emulsion. The aqueous phase consisted of the following components:
   0.70% by weight of emulsion of a cationic quick set imidazoline emulsifier (Anova 1620 manufactured by Cargill)
   2.0% by weight of emulsion of Latex (UltraPave)
   HCl in sufficient content to achieve a pH of 2.6

The content of Polymerized Oil will vary depending on the grade of the base oil and the final desired properties.

Example 3: Cationic Emulsion of Asphalt Containing Sulfurized Soybean Oil Blend #2

This example demonstrates the use of another polymerized oil that may be used in applications similar to that described in Example #1.

A modified asphalt binder comprising:
- 95.0% by weight of neat asphalt binder graded as PG64-22 (PG 64.88-24.7)
- 5.0% by weight of a blend having:
  - 14.5% by weight of a sulfurized soybean oil reacted with 7.0% by weight of elemental sulfur at 160° C. for 19 hrs under a Nitrogen sparge. This resulted in a modifier with 70.8% oligomers
  - 85.5% by weight of straight soybean oil
  - Blend of the sulfurized oil and the straight soybean oil had about 16.59% oligomer content and a PDI of approximately 2.44.

The modifier was blended into the asphalt after the binder had been annealed at 150° C. for 1 hour.

The modified asphalt was used as the oil phase in a latex modified cationic rapid set emulsion. The oil phase was 65.0% by total weight of the emulsion. The aqueous phase consisted of the following components:
- 0.70% by weight of emulsion of a cationic quick set imidazoline emulsifier (Anova 1620 manufactured by Cargill)
- 2.0% by weight of emulsion of Latex (UltraPave)
- HCl in sufficient content to achieve a pH of 2.6

The content of Polymerized Oil will vary depending on the grade of the base oil and the final desired properties.

Example 4: Anionic Emulsion of Asphalt Containing Sulfurized Soybean Oil Blend #2

A modified asphalt binder comprising:
- 97.5% by weight of neat asphalt binder graded as PG58-28
- 2.5% by weight of the polymerized oil of Example #3.

The modifier was blended into the asphalt after the binder had been annealed at 150° C. for 1 hour.

The modified asphalt was used as the oil phase in a latex modified anionic rapid set emulsion. The oil phase was 67% by total weight of the emulsion. A rapid setting anionic aqueous phase, typically used for RS2-P type emulsions was utilized. The emulsion can be used in rapid setting applications such as chip seals, fog seals, and sand seals. The content of Polymerized Oil will vary depending on the grade of the base oil and the final desired properties.

Example 5: Cationic Emulsion of Sulfurized Soybean Oil Blend #1

An oil in water cationic emulsion was made using the polymerized oil of Example #1 as the "oil phase." The oil phase was 50% by total weight of the emulsion. The aqueous phase consisted of the following components:
- 0.5% by weight of emulsion of a cationic rapid set emulsifier (AA-89, manufactured by MeadWest Vaco).
- HCl in sufficient content to achieve a pH of 2.0-2.2

This formulation is suitable for rejuvenating surface applications used for pavement maintenance and preservation, especially rejuvenating fog seals and sand seals. Furthermore, the emulsified solution enables use in low unheated paving applications (known as "Cold Mixes") such as cold in place recycling, cold patch, and cold mix pavement layers. Use of rapid-setting surfactant formulations, such as that used in this example, enable rapid buildup of aggregate retention and traffic resistance.

Example 6: Cationic Emulsion of Sulfurized Soybean Oil Blend #2

This example demonstrates the use of a quick setting emulsifier in place of a rapid setting emulsifier, for solutions that may be used in applications similar to that described in Example #5.

An oil in water cationic emulsion was made using the following polymerized oil as the "oil phase":
- 59.0% by weight of a sulfurized soybean oil reacted with 7.0% by weight of elemental sulfur at 160° C. for 19 hrs under a Nitrogen sparge. This resulted in a modifier with 70.8% oligomer
- 41.0% by weight of straight soybean oil
- Blend of the sulfurized oil and the soybean oil had about 45.6% oligomer content and a PDI of approximately 3.95.

The oil phase was 50% by total weight of the emulsion. The aqueous phase consisted of the following components:
- 0.5% by weight of emulsion of a cationic quick set imidazoline emulsifier (Anova 1620 manufactured by Cargill)
- HCl in sufficient content to achieve a pH of 2.0-2.2

Example 7: Cationic Emulsion of Sulfurized Soybean Oil Blend #3

This example demonstrates the use of another polymerized oil, for solutions that may be used in applications similar to that described in Example #5.

An oil in water cationic emulsion was made using the following polymerized oil as the "oil phase":
- 14.5% by weight of a sulfurized soybean oil reacted with 7.0% by weight of elemental sulfur at 160° C. for 19 hrs under a Nitrogen sparge. This resulted in a modifier with 70.8% oligomers
- 85.5% by weight of straight soybean oil
- Blend of the sulfurized oil and the straight soybean oil had about 17% oligomer content The oil phase was 50% by total weight of the emulsion. The aqueous phase consisted of the following components:
- 0.5% by weight of emulsion of a cationic quick set imidazoline emulsifier (Anova 1620 manufactured by Cargill)
- HCl in sufficient content to achieve a pH of 2.0-2.2

Example 8: Cationic Emulsion of Sulfurized Soybean Oil and Recovered Corn Oil Blend #1

This example demonstrates the use of another polymerized oil, for solutions that may be used in applications similar to that described in Example #5.

An oil in water cationic emulsion was made using the following polymerized oil as the "oil phase":
- 59.0% by weight of a sulfurized soybean oil reacted with 7.0% by weight of elemental sulfur at 160° C. for 19 hrs under a Nitrogen sparge. This resulted in a modifier with 70.8% oligomer 41.0% by weight of recovered corn oil Blend of the sulfurized oil and the recovered corn oil had about 46.31% oligomer content and a PDI of approximately 4.40.

The oil phase was 50% by total weight of the emulsion. The aqueous phase consisted of the following components:

0.5% by weight of emulsion of a cationic quick set imidazoline emulsifier (Anova 1620 manufactured by Cargill)

HCl in sufficient content to achieve a pH of 2.0-2.2

Example 9: Cationic Emulsion of Sulfurized Soybean Oil and Recovered Corn Oil Blend #2

This example demonstrates the use of another polymerized oil, for solutions that may be used in applications similar to that described in Example #5.

An oil in water cationic emulsion was made using the following polymerized oil as the "oil phase":

14.5% by weight of a sulfurized soybean oil reacted with 7.0% by weight of elemental sulfur at 160° C. for 19 hrs under a Nitrogen sparge. This resulted in a modifier with 70.8% oligomer 85.5% by weight of recovered corn oil Blend of the sulfurized oil and the recovered corn oil had about 16.03% oligomer content and a PDI or approximately 3.28.

The oil phase was 50% by total weight of the emulsion. The surfactant phase consisted of the following components:

0.5% by weight of emulsion of a cationic quick set imidazoline emulsifier.

HCl in sufficient content to achieve a pH of 2.0-2.2.

Example 10: Cationic Emulsion of Sulfurized Soybean Oil and Recovered Corn Oil Blend #1

This example demonstrates the use of a triethylamine (TEA) as an emulsifier, utilizing the acid functionality of the recovered corn oil (AV of approximately 30 mg KOH/g) to produce a surfactant. The resulting product may be used in applications similar to that described in Example #5.

An oil in water cationic emulsion was made using the following polymerized oil as the "oil phase". The oil phase was 50% by total weight of the emulsion.

59.0% by weight of a sulfurized soybean oil reacted with 7.0% by weight of elemental sulfur at 160° C. for 19 hrs under a Nitrogen sparge. This resulted in a modifier with 70.8% oligomer 41.0% by weight of recovered corn oil Blend of the sulfurized oil and the recovered corn oil had about 46.31% oligomer content and a PDI of approximately 4.40.

TEA was added at 0.75% by weight of the polymerized oil and blended into the oil phase Example 11: Cutback of Sulfurized Soybean Oil Blend Using Soy Methyl Ester A "cutback" formulation was made using Soy Methyl Ester and a polymerized oil. This product is suitable for use in low temperature and unheated paving applications (known as "Cold Mixes") such as cold in place recycling, cold patch, and cold mix pavement layers.

The cutback contained the following material, blended at 60° C.:

59.0% by weight of a sulfurized soybean oil reacted with 7.0% by weight of elemental sulfur at 160° C. for 19 hrs under a Nitrogen sparge. This resulted in a modifier with 70.8% oligomer 8.5% by weight of straight soybean oil 32.3% by weight of Soy Methyl Ester The resulting cutback blend of the sulfurized oil had the following properties:

Oligomer content of about 50.1%

PDI of approximately 4.12

Density at 25° C. of 0.934 g/ml

Viscosity at 40° C. of 90.4 cSt

Viscosity at 25 C of 150 cSt

The invention claimed is:

1. A rejuvenating composition for asphalt applications, comprising a polymerized oil comprising a starting oil material crosslinked with elemental sulfur, the polymerized oil having a polymeric distribution ranging from about 2 to about 80 wt % oligomer content and a Hildebrand solubility ranging from about 6 to about 12.

2. The composition of claim 1, further comprising asphalt.

3. The composition of claim 1, further comprising recycled asphalt.

4. The composition of claim 1, further comprising a biorenewable oil or petroleum based oil.

5. The composition of claim 1, further comprising a modified oil.

6. The composition of claim 1, further comprising thermoplastic elastomeric and plastomeric polymers, polyphosphoric acid, anti-stripping additives, wan mix additives, emulsifiers and/or fibers.

7. The composition of claim 1, wherein the crosslinking comprises heating to about 130° C. to about 250° C.

8. The composition of claim 1, wherein the crosslinking comprises heating to about 130° C. to about 220° C.

9. The composition of claim 1, wherein the crosslinking comprises heating to about 160° C. to about 200° C.

10. The composition of claim 1, wherein the polymerized oil has a sulfur content of 0.01 wt % to 8 wt %.

11. The composition of claim 1, wherein the composition is an emulsion.

12. The composition of claim 11, further comprising asphalt.

13. The composition of claim 11, further comprising recycled asphalt.

14. The composition of claim 11, further comprising thermoplastic elastomeric and plastomeric polymers, polyphosphoric acid, anti-stripping additives, warm mix additives, emulsifiers and/or fibers.

15. A method comprising applying the composition of claim 11 to an existing pavement surface.

16. A method comprising applying the composition of claim 14 to treat RAS or RAP and further mixing the treated RAS or RAP with virgin asphalt thereby obtaining a rejuvenated asphalt blend.

17. A method comprising applying the composition of claim 1 to an existing pavement surface.

18. A method comprising applying the composition of claim 1 to treat RAS or RAP and further mixing the treated recycled asphalt shingles (RAS) or recycled asphalt pavement (RAP) with virgin asphalt thereby obtaining a rejuvenated asphalt blend.

19. A method comprising applying the composition of claim 1 as part of a cold patching material, a high performance cold patch or cold mix application that contains recycled asphalt thereby obtaining treated RAS or RAP.

20. A method comprising applying the composition of claim 1 to milled asphalt pavement for cold-in-place or hot-in-place recycling of the milled asphalt pavement.

\* \* \* \* \*

UNITED STATES PATENT AND TRADEMARK OFFICE
CERTIFICATE OF CORRECTION

PATENT NO.        : 10,329,426 B2
APPLICATION NO.   : 15/715914
DATED             : June 25, 2019
INVENTOR(S)       : Todd L. Kurth et al.

Page 1 of 1

It is certified that error appears in the above-identified patent and that said Letters Patent is hereby corrected as shown below:

In the Specification

In Column 1, Lines 9-11, delete "This application claims the benefit of U.S. Provisional Application No. 62/126,064 filed on Feb. 27, 2015, which is hereby incorporated by reference in its entirety." and insert -- This application is a Divisional of U.S. Patent Application No. 15/553,711, filed August 25, 2017, entitled "REJUVENATING COMPOSITIONS FOR ASPHALT APPLICATIONS & METHODS OF MANUFACTURING THE SAME", which is a national phase application of International Application PCT/US16/019790, filed February 26, 2016, entitled "REJUVENATING COMPOSITIONS FOR ASPHALT APPLICATIONS & METHODS OF MANUFACTURING THE SAME," which claims the benefit of U.S. Provisional Patent Application, Serial No. 62/126,064, filed February 27, 2015, entitled "POLYMERIZED OILS & METHODS OF MANUFACTURING THE SAME," which is hereby incorporated by reference in its entirety. --, therefor.

In the Claims

In Column 10, Line 31, in Claim 6, delete "wan" and insert -- warm --, therefor.

In Column 10, Line 54, in Claim 16, delete "14" and insert -- 11 --, therefor.

Signed and Sealed this
First Day of October, 2019

Andrei Iancu
*Director of the United States Patent and Trademark Office*